United States Patent
Inglese et al.

(10) Patent No.: US 11,426,062 B2
(45) Date of Patent: Aug. 30, 2022

(54) INTRA-ORAL 3-D FLUORESCENCE IMAGING

(71) Applicant: Carestream Health, Inc., Rochester, NY (US)

(72) Inventors: Jean-Marc Inglese, Bussy-Saint-Georges (FR); Wei Wang, Shanghai (CN); Victor C. Wong, Rochester, NY (US); Guijian Wang, Shanghai (CN); Larry A. Greenspan, Sparks, MD (US); Mark Woodman, Northhill (GB)

(*) Notice: Subject to any disclaimer, the term of this patent is extended or adjusted under 35 U.S.C. 154(b) by 180 days.

(21) Appl. No.: 15/528,773

(22) PCT Filed: Dec. 17, 2014

(86) PCT No.: PCT/US2014/070719
§ 371 (c)(1),
(2) Date: May 23, 2017

(87) PCT Pub. No.: WO2016/099471
PCT Pub. Date: Jun. 23, 2016

(65) Prior Publication Data
US 2017/0319057 A1    Nov. 9, 2017

(51) Int. Cl.
*A61B 1/24*      (2006.01)
*A61B 1/00*      (2006.01)
(Continued)

(52) U.S. Cl.
CPC ............ *A61B 1/24* (2013.01); *A61B 1/00009* (2013.01); *A61B 1/043* (2013.01); *A61B 1/0638* (2013.01);
(Continued)

(58) Field of Classification Search
CPC ... A61B 1/00009; A61B 1/043; A61B 1/0638; A61B 1/24; A61B 5/0071; A61B 5/0088;
(Continued)

(56) References Cited

U.S. PATENT DOCUMENTS

| | | |
|---|---|---|
| 4,479,499 A | 10/1984 | Alfano |
| 4,515,476 A | 5/1985 | Ingmar |

(Continued)

FOREIGN PATENT DOCUMENTS

| | | |
|---|---|---|
| CN | 106999020 A | 8/2017 |
| EP | 3 232 898 A1 | 10/2017 |

(Continued)

OTHER PUBLICATIONS

First Office Action received for Chinese Patent Application Serial No. 201480083987.6, dated Feb. 5, 2018, 21 pages (including English Translation).

(Continued)

*Primary Examiner* — Edward Park
(74) *Attorney, Agent, or Firm* — Alston & Bird LLP

(57) ABSTRACT

Method and apparatus embodiments can generate a volume fluorescence image of a tooth. Method and apparatus embodiments can project structured light patterns onto a tooth and generate a contour (volume) image of the tooth surface from acquired corresponding structured light projection images; then acquire one or more fluorescence images of the tooth generated under blue-UV illumination. A composite image that shows fluorescence image content mapped to the generated contour image can be transmitted, stored, modified and/or displayed.

2 Claims, 14 Drawing Sheets

(51) Int. Cl.
*A61B 1/04* (2006.01)
*A61B 5/00* (2006.01)
*A61C 9/00* (2006.01)
*A61B 1/06* (2006.01)

(52) U.S. Cl.
CPC .......... *A61B 5/0071* (2013.01); *A61B 5/0088* (2013.01); *A61B 5/7425* (2013.01); *A61C 9/006* (2013.01); *A61C 9/0046* (2013.01); *A61C 9/0053* (2013.01)

(58) Field of Classification Search
CPC ... A61B 5/7425; A61C 9/0046; A61C 9/0053; A61C 9/006
See application file for complete search history.

(56) References Cited

U.S. PATENT DOCUMENTS

| | | | |
|---|---|---|---|
| 6,231,338 B1 | 5/2001 | de Josselin de Jong et al. | |
| 6,359,648 B1 | 3/2002 | Fukasaka | |
| 6,731,783 B2 * | 5/2004 | Tsujii | H04N 5/32 250/582 |
| 7,596,253 B2 | 9/2009 | Wong et al. | |
| 7,668,355 B2 | 2/2010 | Wong et al. | |
| 2004/0202356 A1 | 10/2004 | Stookey et al. | |
| 2004/0240716 A1 | 12/2004 | de Josselin de Jong et al. | |
| 2010/0268069 A1 | 10/2010 | Liang | |
| 2011/0287387 A1 | 11/2011 | Chen et al. | |
| 2012/0189182 A1 * | 7/2012 | Liang | A61C 19/00 382/131 |
| 2014/0161369 A1 * | 6/2014 | Ishihara | A61B 1/043 382/274 |

FOREIGN PATENT DOCUMENTS

| | | |
|---|---|---|
| JP | 2017-537744 A | 12/2017 |
| KR | 10-2017-0097653 A | 8/2017 |
| WO | 2014/000745 A1 | 1/2014 |
| WO | WO 2014/000745 A1 * | 1/2014 |
| WO | 2015/011173 A1 | 1/2015 |
| WO | 2016/099471 A1 | 6/2016 |

OTHER PUBLICATIONS

Communication pursuant to Article 94(3) EPC issued in EP Patent Application No. 14824689.5, dated Mar. 26, 2018, 5 pages.
International Preliminary Report On Patentability cited in corresponding International Application No. PCT/US2014/070719 dated Jun. 29, 2017, 9 pages.
International Search Report, International application No. PCT/US2014/070719, dated Jul. 16, 2015, 2 pages.

* cited by examiner

INTRA-ORAL 3-D FLUORESCENCE IMAGING

CROSS REFERENCE TO RELATED APPLICATIONS

This application claims the benefit of and is a U.S. National Phase filing of PCT Application PCT/US2014/070719 filed Dec. 17, 2014, entitled "INTRA-ORAL 3-D FLUORESCENCE IMAGING", in the name of Inglese et al. which is incorporated herein by reference in their entirety.

FIELD OF THE INVENTION

The invention relates generally to dental imaging and more particularly to apparatus and methods for providing 3-D contour images that can include images from tooth fluorescence.

BACKGROUND OF THE INVENTION

Conventional 2-D imaging has been used, with considerable success, for intra-oral applications. However, because of the particular constraints and features of the mouth, it is recognized that 2-D imaging has some significant limitations for showing tooth structure and cannot provide the level of detail and depth information that would be available with a 3-D image, or an image that at least provided reasonable representation of tooth contour.

Fringe projection imaging uses patterned or structured light to obtain surface contour information for structures of various types. In fringe projection imaging, a pattern of lines of an interference fringe or grating is projected toward the surface of an object from a given direction. The projected pattern from the surface is then viewed from another direction as a contour image, taking advantage of triangulation in order to analyze surface information based on the appearance of contour lines. Phase shifting, in which the projected pattern is incrementally spatially shifted for obtaining additional measurements at the new locations, is typically applied as part of fringe projection imaging, used in order to complete the contour mapping of the surface and to increase overall resolution in the contour image.

Fringe projection imaging has been used effectively for surface contour imaging of solid, highly opaque objects and has been used for imaging the surface contours for some portions of the human body and for obtaining detailed data about skin structure. Teeth present a particular challenge for contour imaging, due to factors such as relative translucency of the tooth and scattering by the tooth material, irregularities in shape and structure, and difficulties in providing sufficient light to surfaces disposed at very different angles.

Structured light imaging techniques more accurately represent tooth contour and overall shape, but do not provide significant information related to the condition of the tooth, such as whether or not caries can be detected. In response to the need for improved caries detection methods, there has been considerable interest in improved imaging techniques that do not employ x-rays.

A number of methods for showing tooth condition employ fluorescence, wherein teeth are illuminated with high intensity blue, violet, or UV light and information is obtained from materials in the tooth that are excited by the illumination energy. This technique, termed quantitative light-induced fluorescence (QLF) by some researchers, operates on the principle that sound, healthy tooth enamel yields a higher intensity of fluorescence under excitation from some wavelengths than does de-mineralized enamel that has been damaged by caries infection. The correlation between mineral loss and loss of fluorescence for blue light excitation is then used to identify and assess carious areas of the tooth. A different relationship has been found for red light excitation, a region of the spectrum for which bacterial by-products in carious regions absorb and fluoresce more pronouncedly than do healthy areas.

While fluorescence can provide useful information on tooth condition, fluorescent images themselves are 2-D images. It can be appreciated that there would be value in presenting fluorescence image results along with at least some amount of contour information about the tooth.

SUMMARY OF THE INVENTION

An aspect of this application is to advance the art of medical imaging, particularly for dental intra-oral imaging applications.

Another aspect of this application is to address, in whole or in part, at least the foregoing and other deficiencies in the related art.

It is another aspect of this application to provide, in whole or in part, at least the advantages described herein.

It is an object of the present invention to advance the art of intra-oral imaging, particularly with respect to processing and presentation of fluorescence image content. Embodiments of the present invention combine features of both contour imaging and fluorescence imaging in order to provide enhanced information about the condition of a patient's teeth and mouth.

An advantage offered by apparatus and/or method embodiments of the application relates to generating a three dimensional representations of teeth and/or gums including fluorescence information.

An advantage offered by apparatus and/or method embodiments of the application relates to projecting a structured light pattern onto the tooth and acquiring a plurality of fluorescence projection images of the tooth and/or generating a contour image of a tooth surface from an acquired plurality of fluorescence projection images.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to an aspect of the application, there is provided a method for obtaining an image of a tooth executed at least in part by a computer processor that can include projecting a structured light pattern onto the tooth and acquiring a plurality of structured light projection images of the tooth; generating a contour image of the tooth surface from the acquired plurality of structured light projection images; acquiring one or more fluorescence images of the tooth generated under blue-UV illumination; and displaying a composite image that shows fluorescence image content mapped to the generated contour image.

According to an aspect of the application, there is provided a method for obtaining an image of a tooth executed at least in part by a computer processor that can include projecting a structured light pattern onto the tooth and acquiring a plurality of fluorescence projection images of the tooth; generating a contour image of the tooth surface from the acquired plurality of fluorescence projection images; and displaying the generated contour image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 2C is a schematic diagram showing a camera in which a fringe pattern generator is in the illumination path for internal light sources.

DESCRIPTION OF EXEMPLARY EMBODIMENTS

Figure 1:
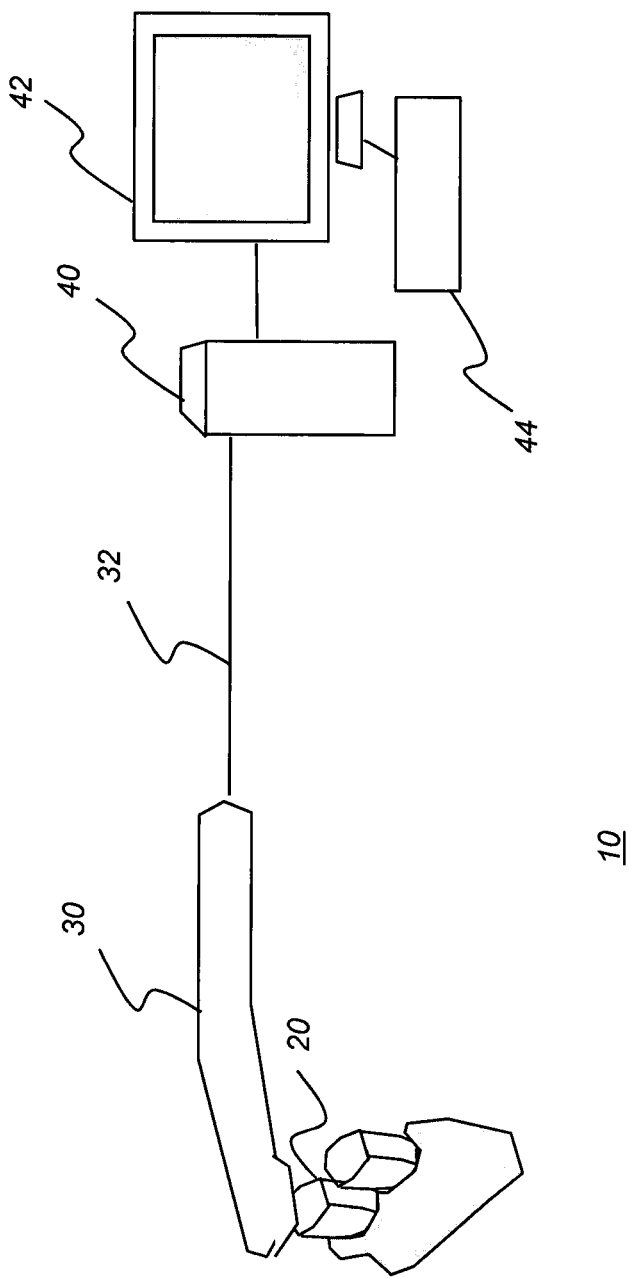
FIG. 1 is a schematic diagram that shows components of an exemplary intra-oral imaging apparatus embodiment according to the application.

The following is a description of exemplary embodiments, reference being made to the drawings in which the same reference numerals identify the same elements of structure in each of the several figures.

In the drawings and text that follow, like components are designated with like reference numerals, and similar descriptions concerning components and arrangement or interaction of components already described are omitted. Where they are used, the terms "first", "second", and so on, do not necessarily denote any ordinal or priority relation, but are simply used to more clearly distinguish one element from another.

In the context of the application, the term "optics" is used generally to refer to lenses and other refractive, diffractive, and reflective components used for shaping and directing a light beam.

In the context of the application, the terms "viewer", "operator", and "user" are considered to be equivalent and refer to the viewing practitioner, technician, or other person who views and manipulates an image, such as a dental image, on a display monitor. An "operator instruction" or "viewer instruction" is obtained from explicit commands entered by the viewer, such as by clicking a button on a camera or by using a computer mouse or by touch screen or keyboard entry. The operator instruction can initiate acquisition and processing of a single image or acquisition and processing of a number of different image types needed for generating a composite image, including patterned and flat-field images, from broadband visible and near-UV or blue-UV sources. To help reduce motion artifacts, composite image generation uses a sequence of images acquired within as short a time span as possible, such as immediately following each other in close succession, for example. It is understood that some finite amount of time is required in order for detector 52 to acquire light and to provide image data for each obtained images. Where multiple images are required, they can be obtained in any order and used to generate a composite image. According to an embodiment of the application, generating the composite image occurs only after it is determined that the plurality of structured light projection images and the one or more fluorescence images have been acquired from the same camera position.

The term "highlighting" for a displayed feature has its conventional meaning as is understood to those skilled in the information and image display arts. In general, highlighting uses some form of localized display enhancement to attract the attention of the viewer. Highlighting a portion of an image, such as an individual tooth or a set of teeth or other structure(s) can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast.

An image is displayed according to image data that can be acquired by a camera or other device, wherein the image data represents the image as an ordered arrangement of pixels. Image content may be displayed directly from acquired image data or may be further processed, such as to combine image data from different sources or to highlight various features of tooth anatomy represented by the image data, for example. As used in the context of the application, the terms "image" and "image data" are generally synonymous, with the understanding that these terms relate to either the digital data representation or the physical displayed representation according to context.

The term "at least one of" is used to mean that one or more of the listed items can be selected. The term "about"

indicates that the value listed can be somewhat altered, within some reasonable tolerance, as long as the alteration does not result in nonconformance of the process or structure to the illustrated embodiment. The term "exemplary" indicates that a particular description or instance is used by way of example, rather than implying that it is an ideal.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S.

As used herein, the term "energizable" relates to a device or set of components that perform an indicated function upon receiving power and, optionally, upon receiving an enabling signal.

The term "actuable" has its conventional meaning, relating to a device or component that is capable of effecting an action in response to a stimulus, such as in response to an electrical signal, for example.

The phrase "in signal communication" as used in the application indicates an electrical connection by which two or more devices and/or components are capable of sharing a signal or signals that travel over some type of signal path. Signal communication may be wired or wireless. The signals may be communication, power, data, or energy signals that may communicate information, power, and/or energy from a first device and/or component to a second device and/or component along a signal path between the first device and/or component and second device and/or component. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

Embodiments of the application address the need for improved intra-oral imaging by using combinations of reflectance and fluorescence imaging techniques, along with contour imaging from patterned-light images and mapping of flat-field images to a detected contour structure. Various types of images can be acquired, processed, and displayed, enabling more detailed analysis and assessment of tooth and mouth features to assist in patient diagnosis.

FIG. 1 is a schematic diagram that shows components of an exemplary intra-oral imaging apparatus embodiment. As shown in FIG. 1, an intra-oral imaging apparatus 10 can obtain images of a tooth 20. An intra-oral camera 30 is in signal communication with a control logic processor 40, also termed a computer processor in the application. Signal communication is provided over a cable 32 or, alternately, over a wireless connection (not shown). Processor 40 is in signal communication with a display 42 and an operator interface 44, such as a keyboard for command entry and a mouse or other pointer device. It can be appreciated that processor 40 can be embodied in a number of different ways, with computer processing circuitry internal and/or external to camera 30. In certain exemplary method and/or apparatus embodiments, processor 40 is capable of providing (e.g., with camera 30), onto the illumination path, in close succession and/or during temporally adjacent time periods, flat-field light or patterned illumination from either the visible or blue-UV light sources, in response to an operator instruction.

Figure 2A:
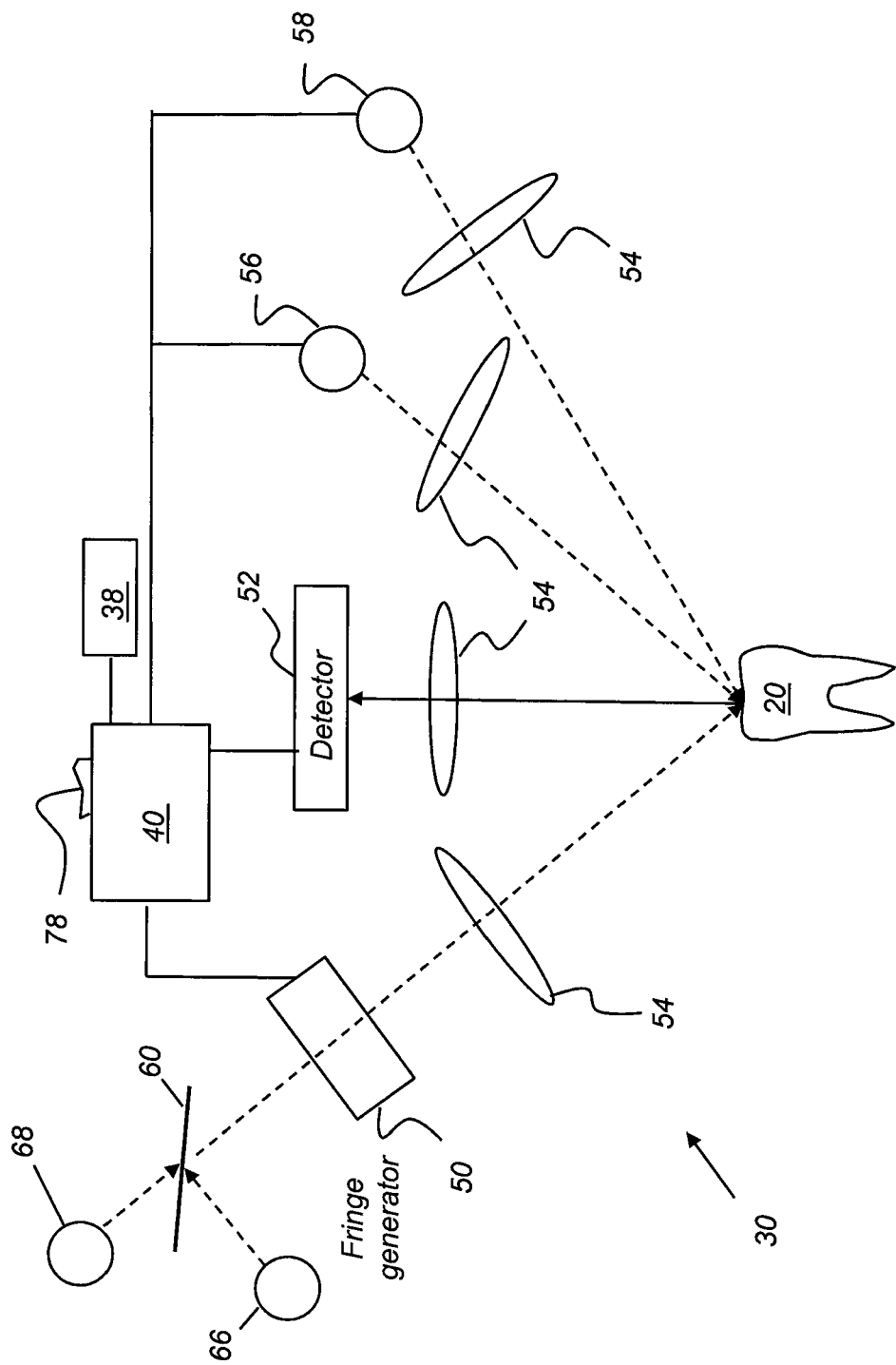
FIG. 2A is a schematic diagram showing exemplary optical components of an intra-oral imaging camera embodiment according to the application.

FIG. 2A is a schematic diagram showing exemplary optical components of an intra-oral imaging camera embodiment according to the application. FIG. 2A shows optical paths for imaging components of one embodiment of intra-oral camera 30 in more detail. Control logic processor 40 may be external to camera 30, as shown in FIG. 1, or may be internal to camera 30. Alternately, processor 40 may use a distributed logic processing arrangement, so that some processing functions are performed within camera 30 and other functions performed by one or more additional processors that acquire data from camera 30. A fringe pattern generator 50 takes light energy from one or more illumination sources, such as a broadband visible or white light source 66 and a second light source 68 for excitation energy that is generally at shorter wavelengths, such as an ultraviolet (UV) or near-ultraviolet or blue source, referred to as a "blue-ultraviolet" or "blue-UV" source in subsequent description. For UV illumination, the emitted light from excitation source 68 is generally below about 410 nm. For blue-UV illumination, the excitation source 68 emits light typically within the range between about 350 nm-500 nm. An advantageous portion of this blue-UV illumination range that is generally effective for exciting visible fluorescence centers approximately about 405 nm. A light combiner 60, such as a beam splitter with a dichroic surface, directs the illumination to the fringe pattern generator 50. Fringe pattern generator 50 may be a spatial light modulator, for example, that is energizable to form one or more patterns of light from light sources 66 and 68 or to form a flat field of light that does not have a pattern for general reflectance or fluorescence imaging. Among types of spatial light modulator that can be used for generating patterned light are digital micromirror arrays, such as the Digital Light Processor from Texas Instruments, Inc., Dallas Tex.; and liquid crystal device (LCD) arrays. Fringe pattern generator 50 can be of a transmissive type (as shown in FIG. 2A) or a reflective type that modulates incident light by reflection (not shown).

A broadband light source 56 provides flat-field white light illumination for reflectance images. A blue-UV source 58 provides flat-field blue-UV illumination for fluorescence imaging. Either or both light sources 56 and 58 can be light emitting diodes (LEDs). Each of the three illumination paths shown in dashed lines and the imaging path to the detector include various optics 54, represented by a lens symbol in FIG. 2A and including lenses, filters, polarizers/analyzers, path-folding optics, apertures, or other components that help to condition and direct the illumination or imaging light appropriately.

Optionally, motion of camera 30 can be determined between images. For example, an optional motion detector 38 or the like can be used to sense motion of camera 30 between images. This information can be used to help correlate image content, both for relating structured light images to each other and for relating fluorescence images to reflectance image content. Alternately, motion can be detected by image analysis software routines executed by control logic processor 40. An optional mode selection switch 78 provides settings that allow operator selection of an imaging mode for intra-oral camera. Switch 78 can allow the selection of a reflectance image capture, fluorescence image capture, or contour image capture using fluorescence or reflectance images and/or combinations thereof. Processor 40 is capable of switching rapidly between the different light sources so that the different types of images can be acquired from the same camera 30 position in close succession, as quickly as detector 52 can process and provide image data output. For any two images taken adjacently, one immediately after the other, image capture is considered to be "in close succession" when the interval between adjacent image acquisitions is determined, more than any other single factor, by the response time required by the system for forming and recording the image data, including component refresh time, for example.

Figure 2B:
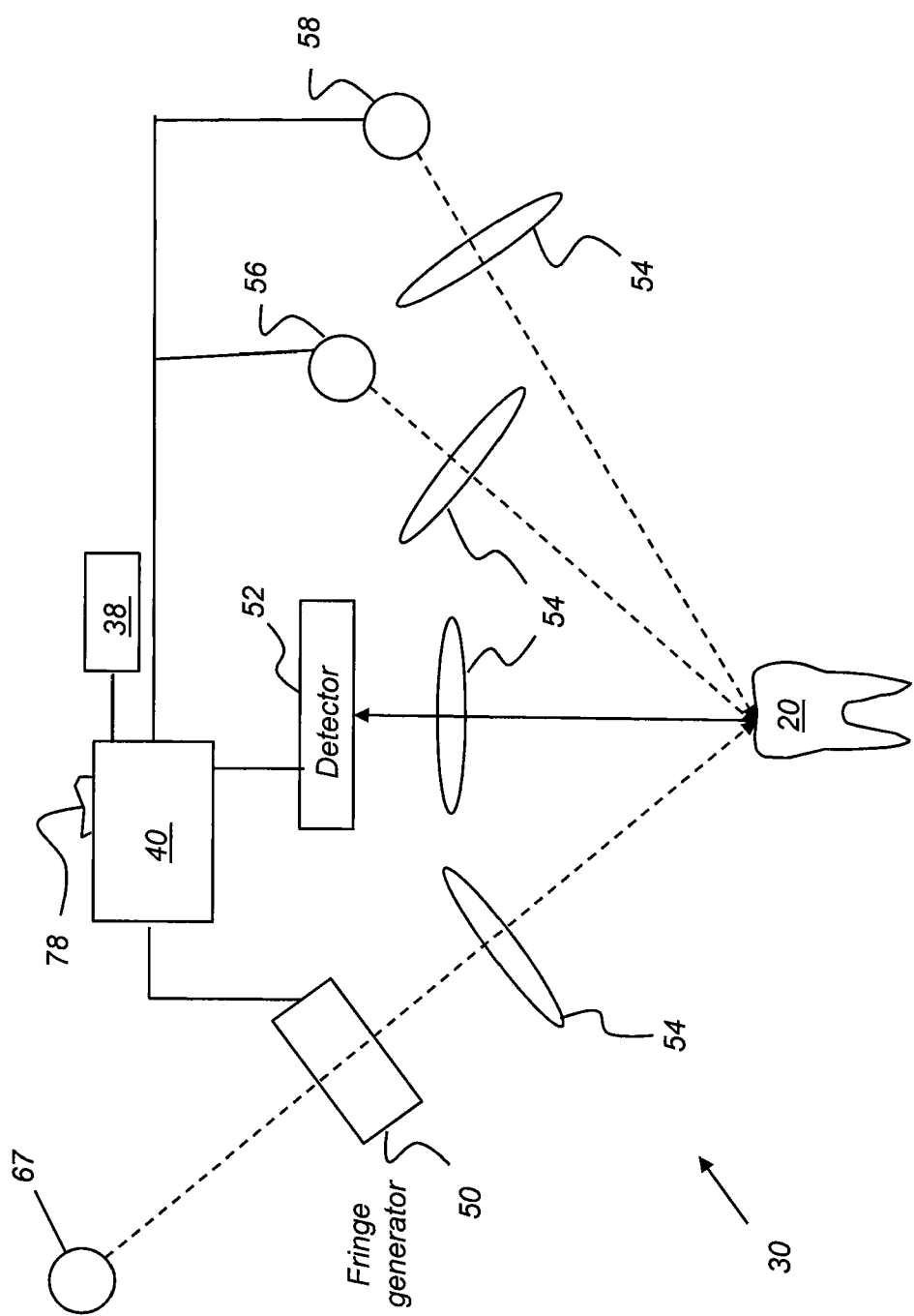
FIG. 2B is a schematic diagram showing another exemplary optical arrangement that uses only a single broadband light source in an intra-oral imaging camera embodiment according to the application.

FIG. 2B is a schematic diagram showing another exemplary optical arrangement in an intra-oral imaging camera embodiment according to the application. FIG. 2B shows a camera 30 embodiment similar to that of FIG. 2A but not using combiner 60, so that only a single light source 67 is used for contour imaging. In this configuration, fringe pattern generator 50 uses light energy from one light source 67, including, but not limited to a broadband visible or white light or blue-UV source. Flat-field illumination for reflectance or fluorescence imaging is provided from light sources 56 or 58 respectively.

Figure 2C:
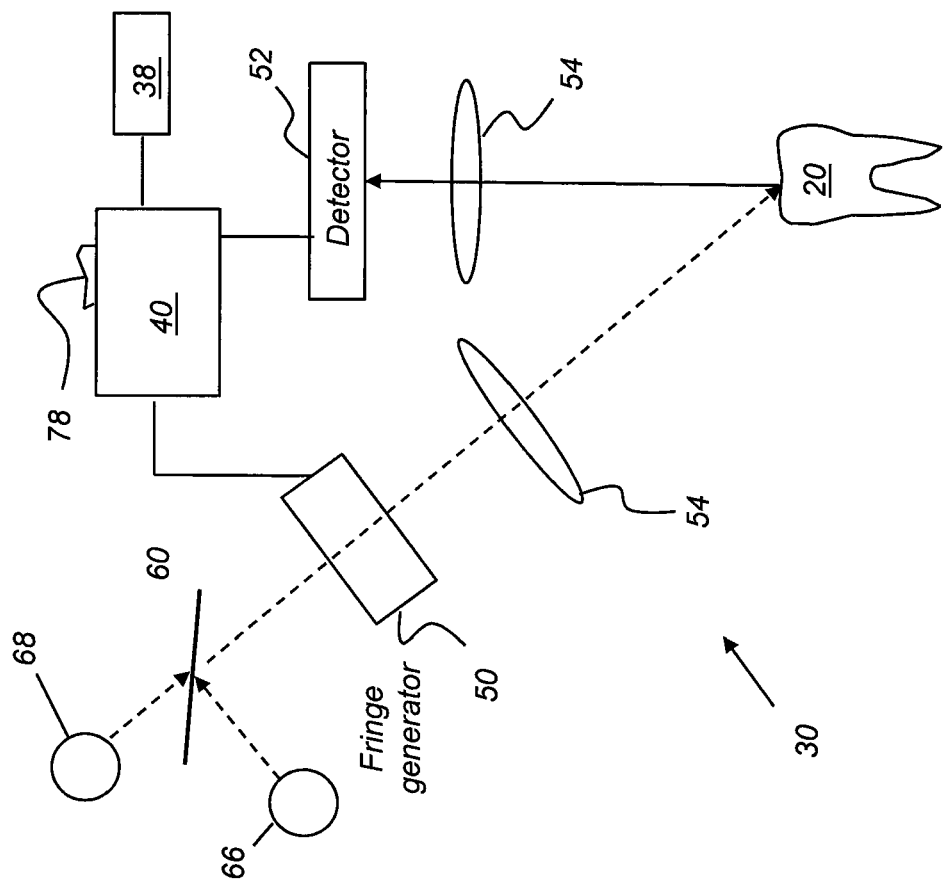
FIG. 2C is a schematic diagram showing another exemplary optical arrangement of an intra-oral imaging camera embodiment in which a fringe pattern generator is in the illumination path for internal light sources according to the application.

FIG. 2C is a schematic diagram showing another exemplary optical arrangement in an intra-oral imaging camera embodiment according to the application. FIG. 2C shows camera 30 embodiment in which fringe pattern generator 50 is in the illumination path for the light sources (e.g., all) within camera 30. Patterned illumination or a flat field of illumination, whether for reflectance or fluorescence imaging or contour imaging, can be formed by a spatial light modulator controlled by processor 40. Spatial light modulators include liquid-crystal devices, or micro-mirror or micro-electromechanical systems (MEMS) devices, for example. An optional motion detector 38 is also included as part of camera 30.

An optional flat field reflectance image can be useful for detecting and showing shade differences between ceramic or other restorations in two or more different restoration areas.

Figure 3:
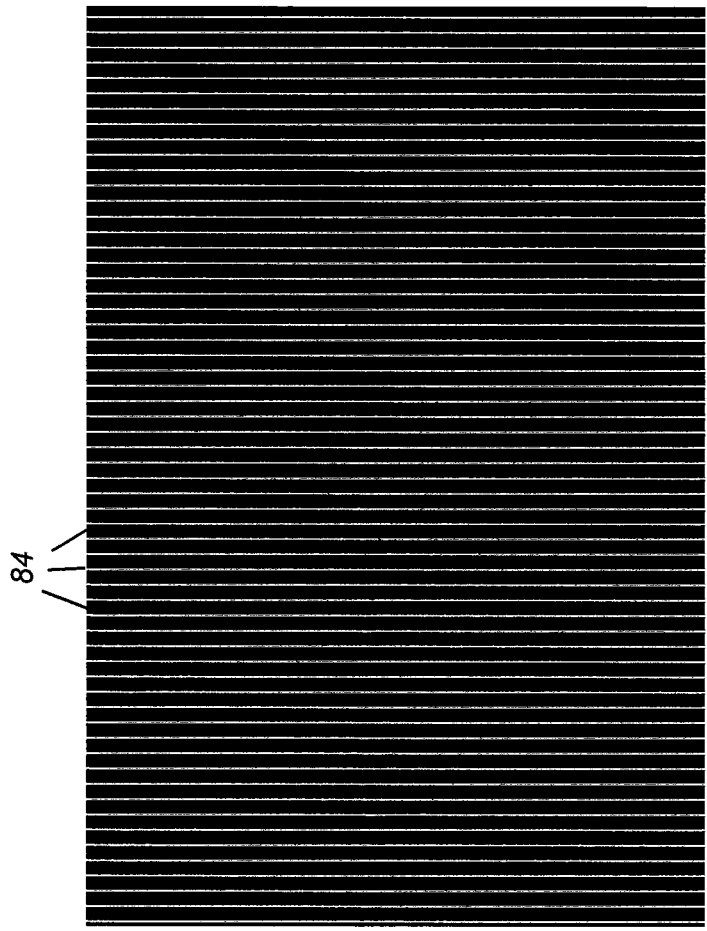
FIG. 3 is a plan view showing a structured light pattern used for contour imaging according to selected embodiments of the application.
Figure 4:
FIG. 4 is an image showing an exemplary structured light pattern projected onto a model of a tooth.

FIG. 3 shows an exemplary structured light pattern 62 that can be generated from fringe pattern generator 50. In this example, structured light pattern 62 is a pattern of parallel lines 84, such as that conventionally used for fringe projection imaging, using techniques familiar to those skilled in the contour imaging arts. More elaborate light patterns can be generated; however, the use of one or more patterns of parallel lines has been shown to be effective in determining surface contour. FIG. 4 shows, on a model tooth structure, how one exemplary structured light pattern 62 can appear on acquired images of teeth.

Figure 5:
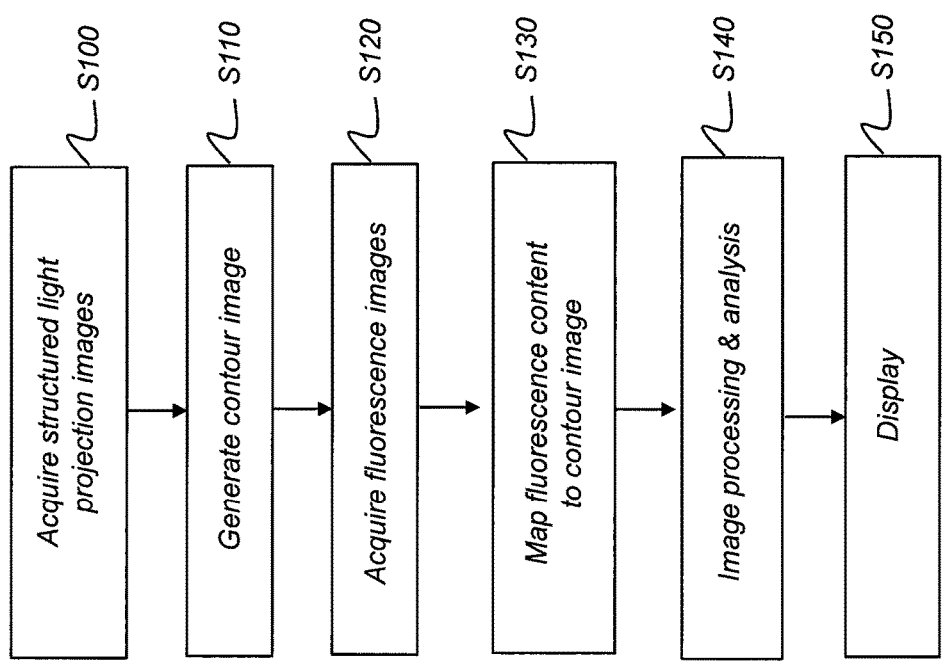
FIG. 5 is a logic flow diagram that shows an exemplary method embodiment for providing fluorescence imaging data correlated with the surface contour of teeth and other oral features according to the application.

FIG. 5 is a logic flow diagram that shows an exemplary method embodiment for providing fluorescence imaging data correlated with surface contour of teeth and/or other oral features according to the application. The logic flow diagram of FIG. 5 shows steps in exemplary process embodiments that can combine fluorescence image content with structure data obtained from contour imaging. In an acquire structured light images step S100, the structured light pattern is projected and corresponding images captured and used for generating surface contour information in a contour image generation step S110. More than one structured light pattern may be projected and imaged for a more complete characterization of surface contour at that imaging perspective. An acquire fluorescence images step S120 can also be executed at or near the same time as step S100. Acquire fluorescence images step S120 directs higher-energy blue-UV illumination to the tooth surface and obtains flat-field fluorescence images that can then be mapped to the contour image in a mapping step S130. Fluorescence images, either contour or flat-field images, can be obtained in video mode. Camera 30 is held in the same position for acquiring contour images and fluorescence images in close succession, with the acquisition speed gated only by the response time required by detector 52 (FIGS. 2A-2C). Following mapping step S130, an optional image processing and analysis step S140 can be performed to aid in caries detection for bacteria activity and demineralization. In addition to caries detection, step S140 can also apply other clinical diagnostics, such as aided detection of tetracyclines. Tetracyclines are known to absorb light in the 320-400 nm UV range. UV excitation from about 358 to 364 nm is particularly effective in allowing detection of nanogram-level quantities of these compounds. Step S130 is optional where only this tetracycline detection function is needed; processing would proceed from step S120 to step S140. Such a resulting image, showing fluorescence image data mapped to the surface contour, is displayed in a display step S150.

It should be noted that imaging steps shown in the FIG. 5 sequence can be executed in any order. Position tracking of camera 30, either using imaging techniques or some other type of position-sensing mechanism, helps to provide the needed correlation between the structured light images and the correlation of the contour image that is generated to fluorescence image data.

Contour image generation from two or more structured light images is known to those skilled in the image processing arts. Contour image generation may use triangulation, camera location or movement compensation, and image analysis in order to obtain surface information from the obtained images.

Figure 6:
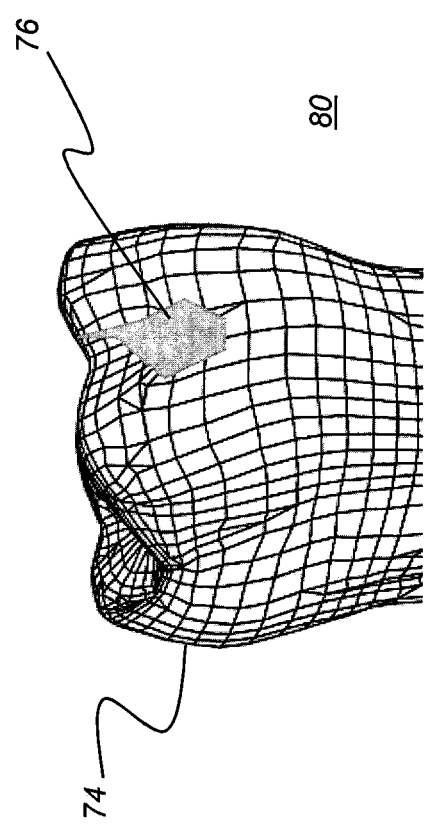
FIG. 6 is a perspective view that shows an exemplary contour image including fluorescence image content according to embodiments of the application.

Mapping step S130 can be executed in a number of ways. According to an embodiment of the application, the fluorescent image is obtained with camera 30 in the same position that is used for obtaining the structured light images. Thus, the same imaging perspective applies for one or more structured light images and one or more corresponding fluorescent image or images. Structured light images and fluorescence image can be obtained in this manner for a number of imaging perspectives, as determined by different camera movements or positions. Then, at each imaging perspective, the same image coordinates can serve for both reconstruction of the contour image and mapping of the fluorescence content to the contour image. FIG. 6 shows, in schematic form, mapping of the fluorescence content to the reconstructed contour image. As an alternative to camera position sensing, mapping processes that utilize image analysis methods can be used. These methods, well known to those skilled in the image processing arts, analyze imaged structures and detect similar features in the obtained images in order to correlate the images to each other.

The fluorescence image content can be analyzed for various conditions. For example, a correlation between mineral loss and loss of fluorescence for blue light excitation can be used to identify and assess carious areas of the tooth. A different relationship has been found for blue or red light excitation regions of the spectrum within which bacterial by-products in carious regions absorb and fluoresce more pronouncedly than do healthy areas.

Applicants note some references related to optical detection of caries.

U.S. Pat. No. 4,515,476 (Ingmar) describes the use of a laser for providing excitation energy that generates fluorescence at some other wavelength for locating carious areas.

U.S. Pat. No. 6,231,338 (de Josselin de Jong et al.) describes an imaging apparatus for identifying dental caries using fluorescence detection.

U.S. Patent Application Publication No. 2004/0240716 (de Josselin de Jong et al.) describes methods for improved image analysis for images obtained from fluorescing tissue.

U.S. Pat. No. 4,479,499 (Alfano) describes a method for using transillumination to detect caries based on the translucent properties of tooth structure.

U.S. Patent Application Publication No. 2004/0202356 (Stookey et al.) describes mathematical processing of spectral changes in fluorescence in order to detect caries in different stages with improved accuracy. Acknowledging the difficulty of early detection when using spectral fluorescence measurements, the '2356 Stookey et al. disclosure describes approaches for enhancing the spectral values obtained, effecting a transformation of the spectral data that is adapted to the spectral response of the camera that obtains the fluorescence image.

In commonly-assigned U.S. Pat. No. 7,668,355 entitled "Method for Detection of Caries" by Wong et al., a method and apparatus that employs both the reflectance and fluorescence images of the tooth is used to detect caries. This method takes advantage of the observed back-scattering, or reflectance, for incipient caries and in combination with fluorescence effects, to provide a dental imaging technique to detect caries.

Certain exemplary apparatus and/or method embodiments of the present invention can utilize fluorescence response in at least two different, overlapping or non-overlapping spectral bands. For example, FIG. 7A shows information that is provided from fluorescence in the green spectral band. Excitation light 70 of blue and near UV wavelengths (nominally centered near about 405 nm according to an embodiment of the application) is directed toward tooth 20 with an outer enamel layer 22 and inner dentine 24. Fluoresced light 72 of green wavelengths, approximately in the range from 500-550 nm, is detected from portions of the tooth 20 having normal mineral content, not exhibiting perceptible damage from decay. In the representation shown in FIG. 7A, a demineralized area 26 is more opaque than healthy enamel and tends to block the incident excitation light 70 as well as to block back-scattered fluorescent light from surrounding enamel. This effect is used by the FIRE method described in commonly assigned U.S. Pat. No. 7,596,253 entitled "Method and Apparatus for Detection of Caries" to Wong et al., wherein the fluorescence green channel data in a 2D still image is combined with reflectance image data in a 2D still image to heighten the contrast of caries regions.

Figure 7B:
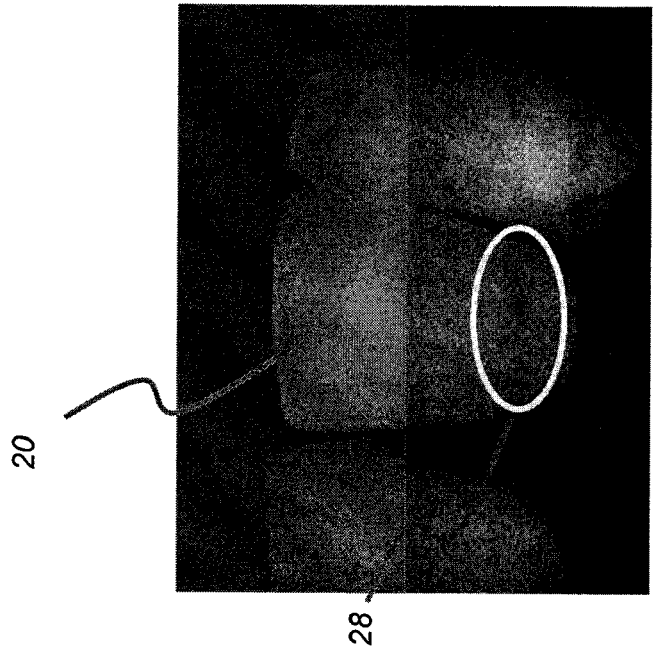
FIG. 7B is an image that shows a demineralization lesion condition detected in a 2D fluorescence image.
Figure 7A:
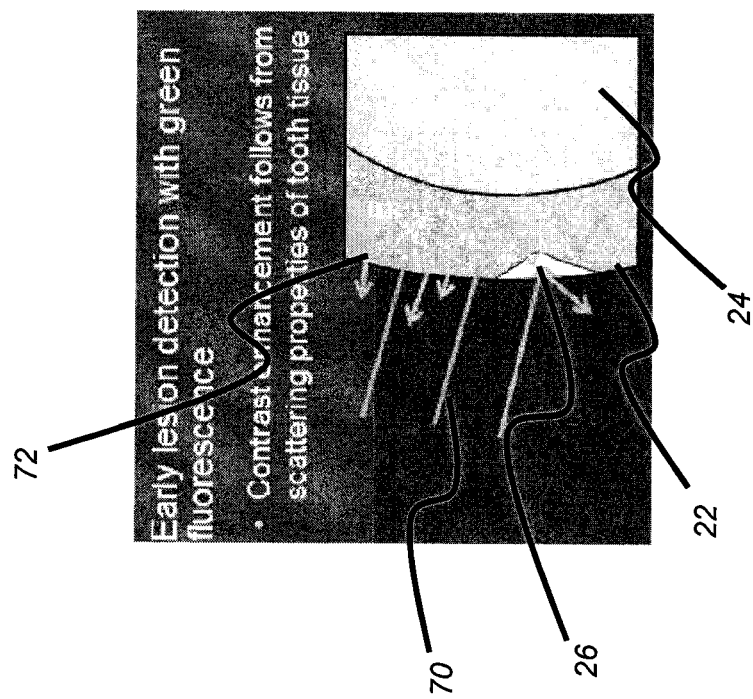
FIG. 7A is a schematic diagram that shows the activity of fluoresced green light for caries detection.

FIG. 7B is a 2D image that shows an early caries condition detected of tooth 20 using the FIRE method. An area 28, circled in FIG. 7B, shows suspected caries with demineralization.

Figure 8B:
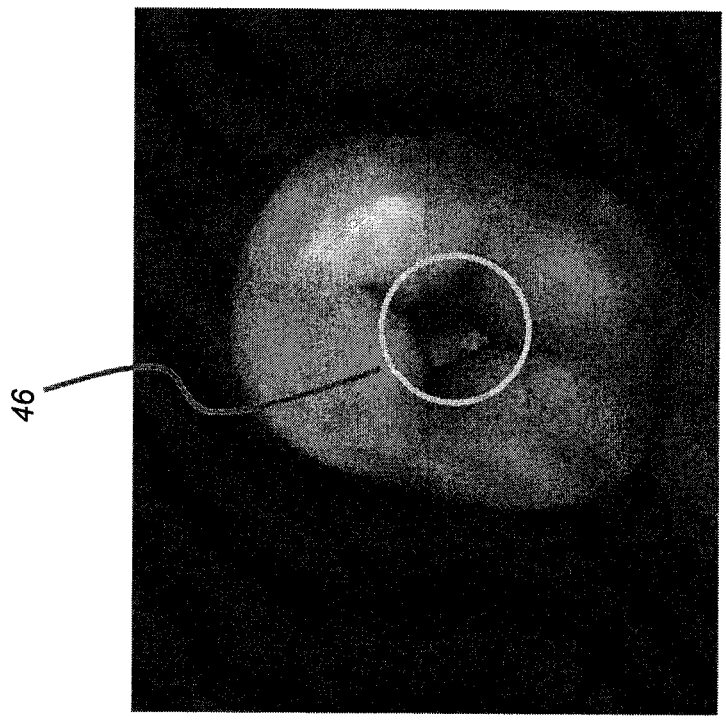
FIG. 8B is a 2D fluorescence image that shows incipient caries detected according to red fluorescence.
Figure 8A:
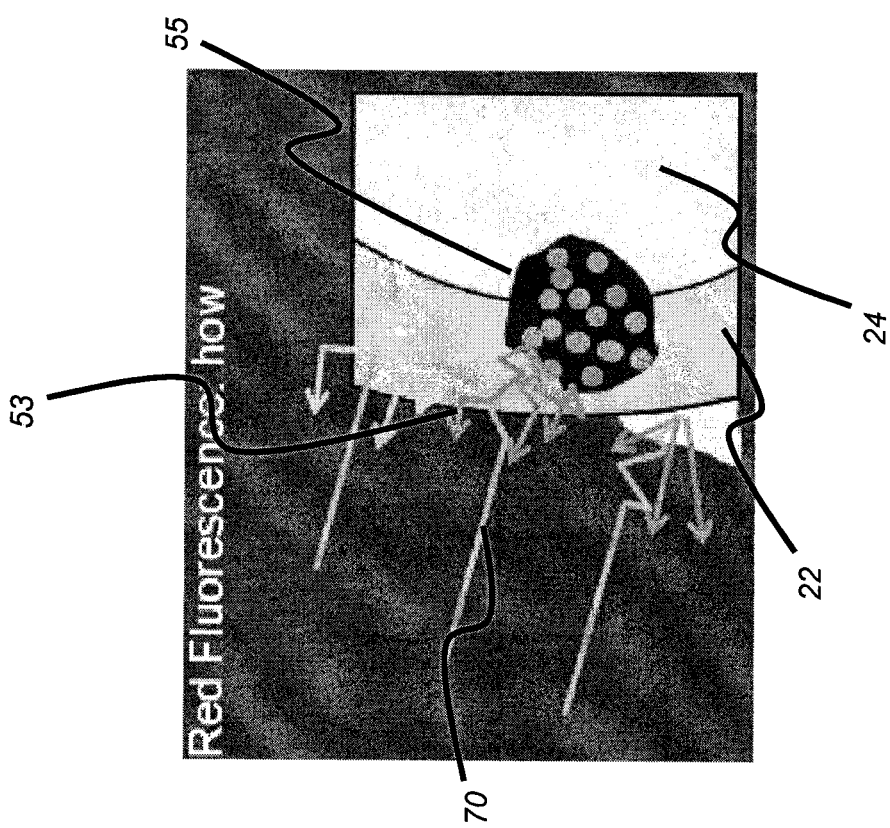
FIG. 8A is a schematic diagram that shows the behavior of fluoresced red light for caries detection.

The fluoresced red light has different significance, for example, indicating the presence of bacterial metabolic products. Bacteria that typically cause a caries lesion, plaque, or tartar typically generate by-products that fluoresce in the red spectrum, above about 600 nm. FIG. 8A shows the behavior of fluoresced red light 53 for caries detection. Here, a caries lesion 55 has significant bacterial activity, evidenced by emission of perceptible amounts of fluoresced light 53 in the red spectral region in response to excitation light 70. With proper filtering of the fluorescent light, this red wavelength emission indicates an active lesion 46, as circled in FIG. 8B.

FIG. 6 is a perspective view that shows an exemplary contour image that can include fluorescence image content (e.g., mapped) according to certain embodiments of the application. FIG. 6 can show an example output of display step S150 (FIG. 5), a composite image 80 with a caries area 76 displayed on a contour image 74. The displayed composite image 80 may include one or more areas of bacterial activity, highlighted according to relative severity or type of bacterial activity that is sensed, such as caries, for example.

Figure 9:
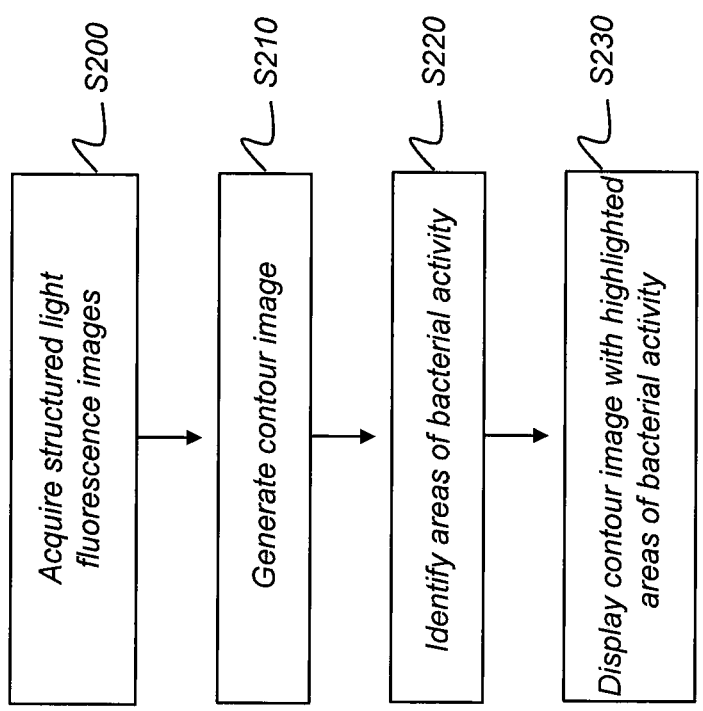
FIG. 9 is a logic flow diagram that shows an exemplary method embodiment for generating and displaying a contour image formed from fluorescence image content according to the application.

According to an alternate apparatus and/or method embodiments of the application, intra-oral imaging apparatus 10 can be used to obtain, process, and display contour images obtained using fluorescence rather than using reflected light. FIG. 9 is a logic flow diagram that shows an exemplary method embodiment for generating and displaying a contour image formed from at least fluorescence image content according to the application. An acquire structured light images step S200 illuminates the tooth or other oral feature with structured light that is intended to excite fluorescence, such as UV or near-UV light. The structured light pattern may be the conventional parallel lines arrangement shown with respect to FIGS. 3 and 4 or may have a different characteristic pattern. Fluoresced light resulting from this illumination pattern is then captured in a set of multiple images, for each of a number of imaging perspectives, in similar manner to that used for reflectance imaging. A contour image can then be formed in a contour image generation step S210. Areas of bacterial activity can be detected from the fluorescent light, as noted previously; this process is performed in an optional identify bacterial areas step S220. A display step S230 can then display the contour image with areas showing bacterial activity highlighted.

It should be noted that imaging steps shown in the FIG. 9 sequence can be executed in any order and can also be executed continuously for dynamic updating. Position tracking of camera 30, either using imaging techniques or some other type of position-sensing mechanism, helps to provide the needed correlation between the structured light images and the correlation of the contour image that is generated to fluorescence image data.

Figure 10:
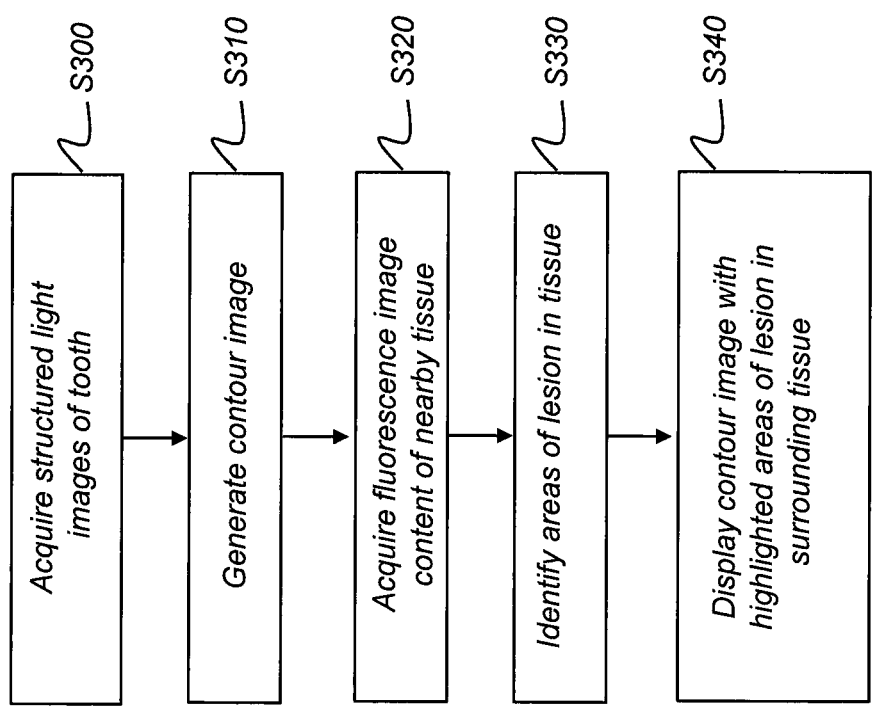
FIG. 10 is a logic flow diagram that shows an exemplary method embodiment for displaying a contour image along with lesion information according to the application.

FIG. 10 is a logic flow diagram that shows an exemplary method embodiment for displaying a contour image along with lesion information in surrounding soft tissue according to the application. FIG. 10 shows a sequence for using a combination of reflectance contour imaging and fluorescence imaging to detect and display areas of lesion in surrounding tissue of the patient's mouth. In an acquire structured light images step S300, a pattern of structured light is projected onto the teeth and tissue two or more times at each of two or more spatially shifted positions to obtain a number of structured light projection images. With camera 30 held at the same position for capture of the patterned light images, a contour image that includes the surrounding tissue can then be formed in a contour image generation step S310. An acquire fluorescence image step S320 then executes, in which fluorescence image content can be obtained from tissue that is near the tooth for which contour information has been obtained. The light for exciting fluorescence can be flat-field light, such as light in the UV or near-UV wavelength range, as described previously. Maintaining camera 30 in the same position allows registration of the fluorescence and contour information. Various sensors (represented as motion detector 38 in FIGS. 2A-2C) can be used to detect inadvertent camera 30 movement; image processing can also be used to determine whether or not camera 30 is in the same position for acquiring the needed images. According to an embodiment of the application, processing for subsequent steps S330 and S340 does not proceed until contour and fluorescence images that can be suitably registered to each other are obtained.

In an identify lesion areas step S330 in the FIG. 10 sequence, image analysis is used to identify tissue areas indicative of lesions. A display step S340 then correlates the imaged tissue locations with imaged teeth and displays identified lesion areas in a composite image. Highlighting of the lesion can be provided for the image displayed as a result of the FIG. 10 sequence.

The sequence shown in FIG. 10 can be used, for example, to aid in detection of mucosal lesions. Lesion detection can use spectral analysis, for example, to identify a suspect area of tissue. It has been observed that excitation of oral mucosa using UV in the range from about 375-440 nm generates fluorescence response from epithelial keratins. Abnormal tissue has reduced fluorescence intensity, indicative of various types of lesions.

It should be noted that image acquisition steps shown in the FIG. 10 sequence can be executed synchronously or in a different order arrangement from that shown, with different image content and corresponding processing updated as new images are acquired. Position tracking of camera 30, either using imaging techniques or some other type of position-sensing mechanism, helps to provide the needed correlation between the structured light images and the correlation of the contour image that is generated to fluorescence image data.

Figure 11:
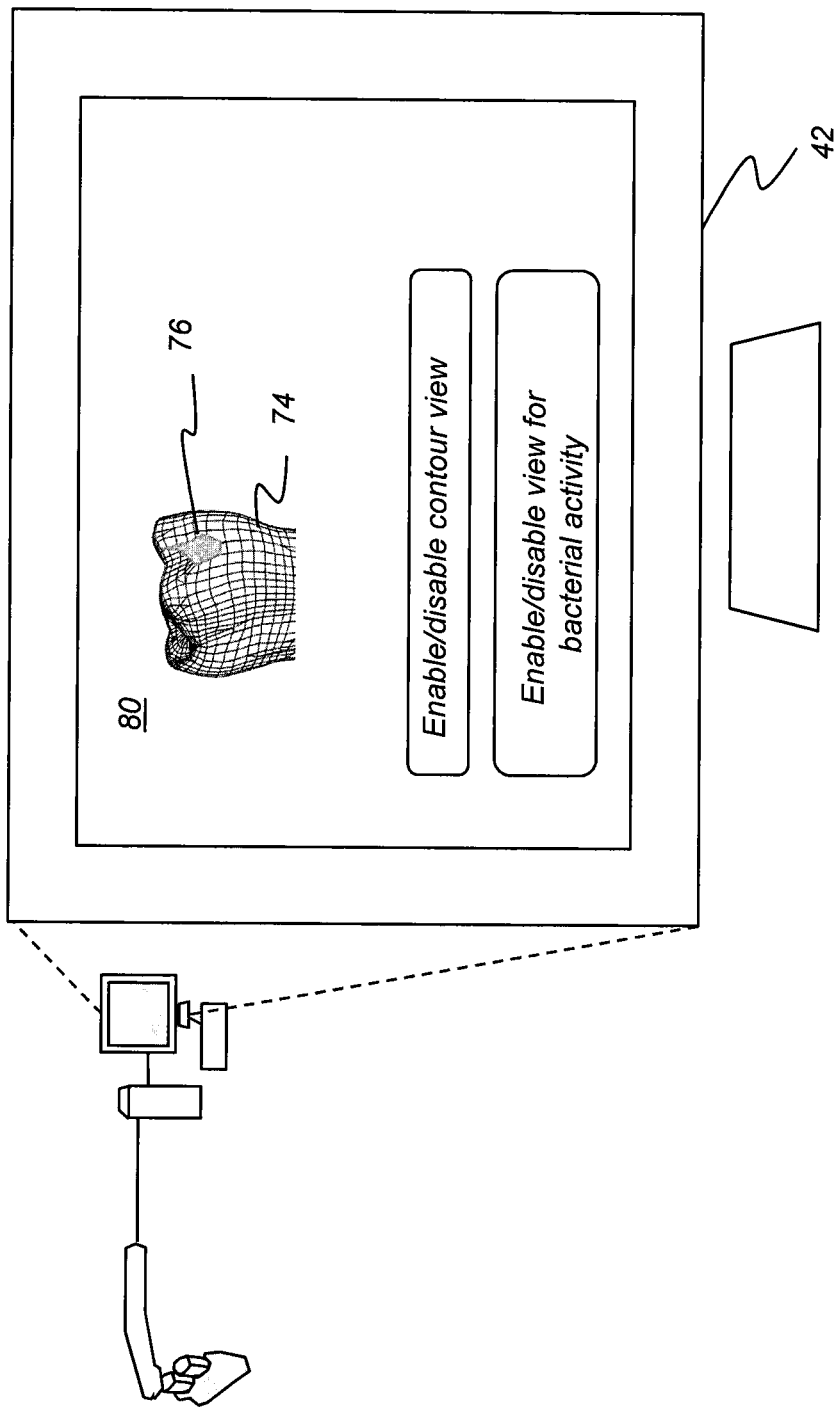
FIG. 11 shows an operator interface for viewing exemplary contour images and mapped data according to certain embodiments of the application.

The processed image content can be presented to the viewer in any of a number of ways. FIG. 11 shows an exemplary operator interface screen on display 42 that allows the viewer to enable or disable display of image content within composite image 80, such as viewing the caries area 76 along with, or separate from, contour image 74, or viewing only contour image 74. This same type of operator interface arrangement can be used for enabling or disabling views of lesions. Pan and zoom image manipulation functions are also available from the operator interface.

Figure 12:
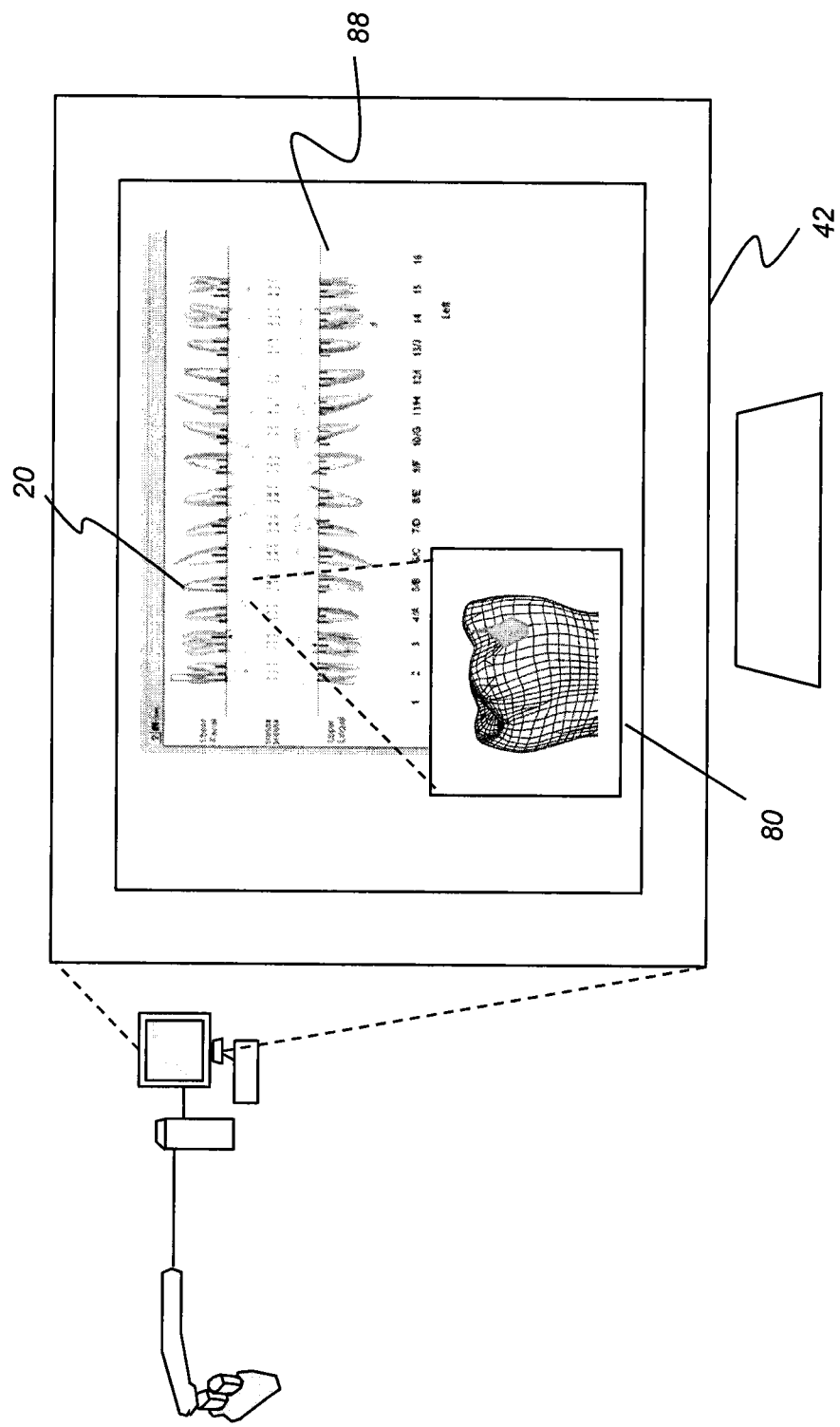
FIG. 12 shows exemplary indexing of a composite image using a displayed dental chart according to certain embodiments of the application.

Embodiments of the application also allow imaged tooth content to be stored in conjunction with dental chart information. FIG. 12 shows an exemplary dental chart 88 on display 42, with composite image 80 contents indexed to a particular tooth 20 according to tooth placement.

In one embodiment, a method for obtaining an image of a tooth can include projecting a structured light pattern onto the tooth and acquiring a plurality of structured light projection images of the tooth; generating a contour image of the tooth surface from the acquired plurality of structured light projection images; acquiring one or more fluorescence images of the tooth generated under blue-UV illumination; generating a composite image having fluorescence image content mapped to the generated contour image according to detected camera movement; identifying one or more restoration areas in the mapped fluorescence image content; and displaying the generated composite image with the one or more identified restoration areas highlighted.

In one embodiment, a method for forming an intra-oral image can include projecting a structured light pattern onto one or more teeth and acquiring a plurality of structured light projection images of the teeth; generating a contour image of the tooth surface from the acquired plurality of structured light projection images; acquiring one or more fluorescence images of the one or more teeth generated under blue-UV illumination; generating a composite image having fluorescence image content for the teeth mapped to the generated contour image; identifying one or more areas of the teeth indicative of tetracycline materials according to the mapped fluorescence image content; and displaying the generated composite image with the one or more identified areas indicative of tetracycline materials highlighted.

In one embodiment, a method for obtaining an intra-oral image can include projecting a structured light pattern onto one or more teeth and at least some portion of the surrounding tissue and acquiring a plurality of structured light projection images of the teeth and surrounding tissue; generating a contour image of the tooth and surrounding tissue surface from the acquired plurality of structured light projection images; acquiring one or more fluorescence images of tissue near the tooth generated under blue-UV illumination; generating a composite image having fluorescence image content for the tissue mapped to the generated contour image; identifying one or more areas indicative of tissue abnormality in the mapped fluorescence image content; and displaying the generated composite image with the one or more identified tissue abnormality areas highlighted.

In one embodiment, an apparatus for intra-oral imaging can include a first broadband visible light source for providing flat-field illumination for reflectance imaging; a blue-UV light source for providing flat-field illumination for fluorescence imaging; a second broadband visible or blue-UV light source for generating a patterned illumination; a fringe pattern generator in the illumination path and energizable to form a projection pattern of light from the second light source for projection onto one or more teeth; a control processor that is energizable to detect when the amount of apparatus motion is below a threshold and to switch between light sources in close succession for obtaining images according to the patterned and flat-field illumination; and a detector in the path of light from the tooth and energizable to form an image according to light in the illumination path.

Consistent with one embodiment, the control logic processor 40 of the present invention is a type of computer processor that utilizes a computer program with stored instructions that perform on image data that has been stored and accessed from an electronic memory. As can be appreciated by those skilled in the image processing arts, a computer program of an embodiment of the present invention can be utilized by a suitable, general-purpose computer system, such as a personal computer or workstation or by a microprocessor device contained within intra-oral camera 30 (FIG. 1). However, many other types of computer systems can be used to execute the computer program of the present invention, including networked processors. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Displaying an image requires memory storage. Display data, for example, is typically stored in a temporary storage buffer that is directly associated with a display device and is periodically refreshed as needed in order to provide displayed data. This temporary storage buffer can also be considered to be a memory, as the term is used in the application. Memory is also used as the data workspace for executing and storing intermediate and final results of calculations and other processing. Computer-accessible memory can be volatile, non-volatile, or a hybrid combination of volatile and non-volatile types.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

What is claimed is:

1. A method for obtaining an image of a tooth, the method executed at least in part by a computer processor and comprising the steps of:

projecting a structured light pattern along a single illumination path onto the tooth and acquiring a plurality of structured light projection images of the tooth;

generating a contour image of the tooth surface from the acquired plurality of structured light projection images;

projecting flat-field illumination using a fluorescence light along the single illumination path onto the tooth and acquiring one or more fluorescence images of the tooth generated under blue-UV illumination;

generating a composite image having fluorescence image content for the tooth mapped to the generated contour image;

identifying one or more areas of the tooth indicative of tetracycline materials according to the mapped fluorescence image content; and displaying the generated composite image that shows fluorescence image content mapped to the generated contour image and with the one or more identified areas indicative of tetracycline materials highlighted.

2. A method for obtaining an image of a tooth, the method executed at least in part by a computer processor and comprising the steps of:

projecting a structured light pattern along a single illumination path onto the tooth and acquiring a plurality of structured light projection images of the tooth, wherein the structured light patterns are also projected onto other teeth and at least some portion of the surrounding tissue and the acquired plurality of structured light projection images also include the other teeth and surrounding tissue;

generating a contour image of the tooth's surface from the acquired plurality of structured light projection images, wherein the generated contour image is of the tooth and surrounding tissue surface from the acquired plurality of structured light projection images;

projecting flat-field illumination using a fluorescence light along the single illumination path onto the tooth and acquiring one or more fluorescence images of the tooth generated under blue-UV illumination, wherein the acquired fluorescence images include tissue near the tooth generated under blue-UV illumination;

generating a composite image having fluorescence image content for the tissue mapped to the generated contour image;

identifying one or more areas indicative of tissue abnormality in the mapped fluorescence image content; and displaying the generated composite image with the one or more identified tissue abnormality areas highlighted and showing fluorescence image content mapped to the generated contour image, wherein the step of generating a composite image occurs only after it is determined that the plurality of structured light projection images and the one or more fluorescence images have been acquired from the same camera position.

* * * * *